(12) United States Patent
Rao et al.

(10) Patent No.: US 12,040,060 B2
(45) Date of Patent: *Jul. 16, 2024

(54) HEALTH CARE SYSTEM TO AID TRIAGE MANAGEMENT

(71) Applicant: ZYTER INC., Rockville, MD (US)

(72) Inventors: Sanjesh Rao, Haymarket, VA (US); Harish Pai, Ashburn, VA (US); Mohamed Madar Mohideen M Z, Chennai (IN)

(73) Assignee: ZYTER INC., Rockville, MD (US)

( * ) Notice: Subject to any disclaimer, the term of this patent is extended or adjusted under 35 U.S.C. 154(b) by 3 days.

This patent is subject to a terminal disclaimer.

(21) Appl. No.: 16/753,088

(22) PCT Filed: Oct. 3, 2018

(86) PCT No.: PCT/US2018/054129
§ 371 (c)(1),
(2) Date: Apr. 2, 2020

(87) PCT Pub. No.: WO2019/070829
PCT Pub. Date: Apr. 11, 2019

(65) Prior Publication Data
US 2020/0279624 A1    Sep. 3, 2020

Related U.S. Application Data

(60) Provisional application No. 62/567,347, filed on Oct. 3, 2017.

(51) Int. Cl.
*G16H 10/60* (2018.01)
*G16H 40/20* (2018.01)
*G16H 50/20* (2018.01)

(52) U.S. Cl.
CPC ............ *G16H 10/60* (2018.01); *G16H 40/20* (2018.01); *G16H 50/20* (2018.01)

(58) Field of Classification Search
CPC ........ G16H 10/60; G16H 40/20; G16H 50/20; G16H 50/30; Y02A 90/10; G06F 19/345;
(Continued)

(56) References Cited

U.S. PATENT DOCUMENTS

2006/0100902 A1* 5/2006 Glimp .................... G16H 10/20
705/2
2011/0082794 A1* 4/2011 Blechman .............. G06Q 10/10
705/50

(Continued)

FOREIGN PATENT DOCUMENTS

| CN | 103905549 A | 7/2014 |
| CN | 106777942 A | 5/2017 |
| CN | 106940757 A | 7/2017 |

OTHER PUBLICATIONS

Extended European Search Report mailed on Jun. 1, 2021 for EP Patent Application No. 18864806.7.

*Primary Examiner* — Alaaeldin M Elshaer
(74) *Attorney, Agent, or Firm* — Raj S. Dave; Dave Law Group LLC

(57) ABSTRACT

According to an aspect of the present disclosure, a healthcare system retrieves multiple parameters relating to a patient from different databases, the parameters including current and historical data relating to the patient. Upon receiving symptoms of a medical problem of the patient, the healthcare system determines based on the symptoms and the multiple retrieved parameters, recommendations to assist in the triage of the patient and provides the recommendations to a healthcare provider to assist in the triage of the patient. Accordingly, the healthcare system is configured to aid triage management by the healthcare system.

20 Claims, 9 Drawing Sheets

(58) Field of Classification Search
CPC . G06F 19/3418; G06F 19/3475; A61B 5/145; A61B 5/00; G06N 5/02; G06N 99/00; G06Q 40/08; G06Q 50/00
USPC .......................................................... 705/2, 3
See application file for complete search history.

(56) References Cited

U.S. PATENT DOCUMENTS

| | | | |
|---|---|---|---|
| 2012/0245952 A1* | 9/2012 | Halterman | G16H 50/20 705/2 |
| 2012/0269420 A1* | 10/2012 | Najarian | A61B 5/412 382/134 |
| 2014/0019162 A1* | 1/2014 | Skowronski | G16H 40/67 705/3 |
| 2014/0244309 A1* | 8/2014 | Francois | G16H 10/60 705/3 |
| 2015/0031321 A1 | 1/2015 | Nakamori et al. | |
| 2015/0089576 A1* | 3/2015 | Poroor | H04L 63/20 726/1 |
| 2015/0154721 A1* | 6/2015 | Thompson | G16H 50/30 705/2 |
| 2015/0221057 A1* | 8/2015 | Raheja | G16H 40/20 705/2 |
| 2015/0332001 A1* | 11/2015 | Goldfein | G16H 40/20 705/3 |
| 2017/0006135 A1* | 1/2017 | Siebel | G06F 16/288 |
| 2017/0011183 A1* | 1/2017 | Valverde, Jr. | G06F 40/169 |
| 2017/0262604 A1* | 9/2017 | Francois | G16H 10/60 |
| 2018/0068083 A1* | 3/2018 | Cohen | G16B 40/20 |
| 2018/0130555 A1* | 5/2018 | Chronis | G06V 10/75 |
| 2018/0218126 A1* | 8/2018 | Salazar | G16H 50/30 |
| 2019/0313992 A1* | 10/2019 | Buelow | G06T 7/68 |

* cited by examiner

| | 511 | 512 | 513 | 514 | 515 | 516 | 517 | 518 |
|---|---|---|---|---|---|---|---|---|
| | Patient ID | Patient Name | HCP ID | HCP Name | Visit Date/Time | Diagnosis | Urgency | Recommendation |
| 541 | PT3007 | Ray, Andrew | HP049 | Joan Ames | 03/07/2017 10:30AM | ...... | ...... | ...... |
| 542 | PT4125 | Feinstein, Clara | HP052 | Anthony Amert | 03/21/2017 11:10AM | ...... | ...... | ...... |
| 543 | PT3018 | Wang, Harry | HP013 | Katie Nelson | 03/29/2017 9:21AM | ...... | ...... | ...... |
| 544 | PT4125 | Feinstein, Clara | HP020 | John Pemberton | 04/01/2017 12:15PM | ...... | ...... | ...... |
| 545 | PT3007 | Ray, Andrew | HP013 | Katie Nelson | 04/09/2017 10:46AM | ...... | ...... | ...... |
| 546 | PT4125 | Feinstein, Clara | HP049 | Joan Ames | 05/06/2017 1:00 PM | ...... | ...... | ...... |
| 547 | PT3018 | Wang, Harry | HP052 | Anthony Amert | 05/06/2017 3:00 PM | ...... | ...... | ...... |

*FIG. 5*

HEALTH CARE SYSTEM TO AID TRIAGE MANAGEMENT

CROSS-REFERENCE TO RELATED APPLICATIONS

This application claims the benefit of priority of U.S. Provisional Application No. 62/567,347, filed Oct. 3, 2017, the content of which is incorporated herein by reference in its entirety.

TECHNICAL FIELD

Embodiments of the present disclosure relate generally to healthcare systems and in particular to use of such systems in aiding triage management.

BACKGROUND

Healthcare systems aid the delivery of various healthcare aspects such as work-flow coordination, records managements, diagnosis, etc., as is well known in the relevant arts. Healthcare systems are often employed by hospitals (healthcare delivery parties, in general) to aid various parties such as the medical staff and patients.

Triage is one of the important aspects of healthcare delivery. As is well known, triage refers to assignment of degrees of urgency in treatment such that the more critical needs can be attended sooner as appropriate. Assignment of degrees of urgency typically involves consideration of the various conditions of the patients to assign appropriate urgency level for treatment of corresponding patients.

Aspects of the present disclosure are directed to management of triage in healthcare systems.

BRIEF SUMMARY

According to an aspect of the present disclosure, a healthcare system retrieves multiple parameters relating to a patient from different databases, the parameters including current and historical data relating to the patient. Upon receiving symptoms of a medical problem of the patient, the healthcare system determines based on the symptoms and the multiple retrieved parameters, recommendations to assist in the triage of the patient and provides the recommendations to a healthcare provider to assist in the triage of the patient. Accordingly, the healthcare system is configured to aid triage management by the healthcare system.

According to one more aspect of the present disclosure, the recommendations provided by the healthcare system also assist in determining a probable diagnosis of the medical problem of the patient. In one embodiment, the recommendations also include (A) diagnostics to be performed for confirmation of the probable diagnosis, (B) drugs suitable for treatment of the probable diagnosis, and (C) specialist healthcare providers having experience in the treatment of the probable diagnosis.

According to yet another aspect of the present disclosure, the healthcare system sends alerts to healthcare providers having responsibility for the patient upon determining that the triage of the patient matches a pre-determined threshold.

In one embodiment, the different databases includes (A) an electronic medical record (EMR) system storing EMRs linked to healthcare providers, each EMR containing information related to a corresponding patient, (B) a cloud database storing data captured using Internet of Things (IoT) devices associated with patients and (C) a monitoring database storing information collected by monitoring devices attached to the patients.

In one embodiment, the current and historical data include records of the patient, lab reports, data from IoT devices, data from monitoring devices, and clinical workflows available at multiple EMR systems. The records of the patient include patient information, symptoms of previous medical problems, details of visits, details of upcoming appointments, doctor's notes, observations, clinical summary, medications, patient documents and care plan.

Several aspects of the invention are described below with reference to examples for illustration. However, one skilled in the relevant art will recognize that the disclosure can be practiced without one or more of the specific details or with other methods, components, materials and so forth. In other instances, well-known structures, materials, or operations are not shown in detail to avoid obscuring the features of the disclosure. Furthermore, the features/aspects described can be practiced in various combinations, though only some of the combinations are described herein for conciseness.

While the features of the present disclosure are described substantially in the context of healthcare services, it should be appreciated that several aspects of the present disclosure can be applied to other industries such as banking, telecommunication, transport, education and retail services.

BRIEF DESCRIPTION OF THE DRAWINGS

Example embodiments of the present disclosure will be described with reference to the accompanying drawings briefly described below.

FIG. 5 depicts portions of a visit summary data specifying the details of interactions between patients and healthcare providers in one embodiment.

In the drawings, like reference numbers generally indicate identical, functionally similar, and/or structurally similar elements. The drawing in which an element first appears is indicated by the leftmost digit(s) in the corresponding reference number.

DETAILED DESCRIPTION OF THE EMBODIMENTS OF THE DISCLOSURE

1. Example Environments

Figure 1B:
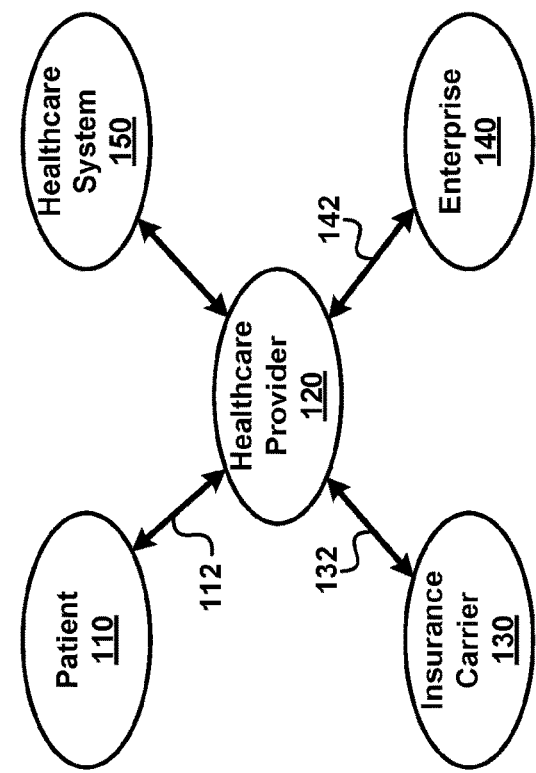
FIGS. 1A-1C depicts example environments in which several aspects of aiding triage management in healthcare systems can be implemented.
Figure 1A:
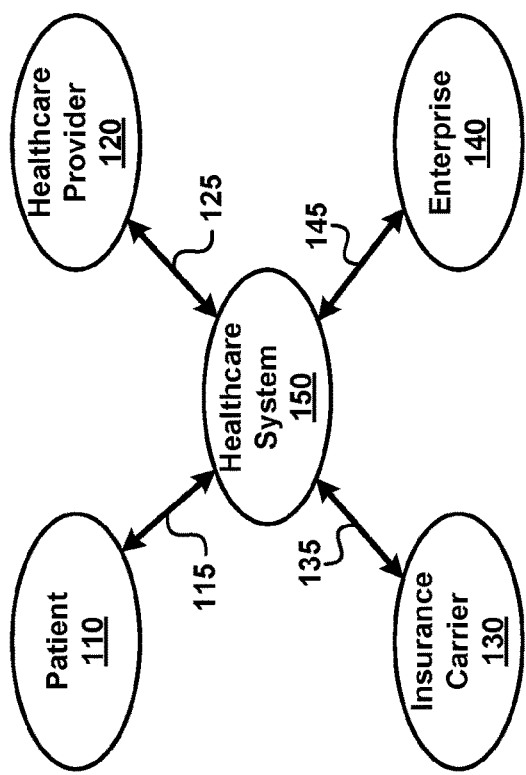
Figure 1C:
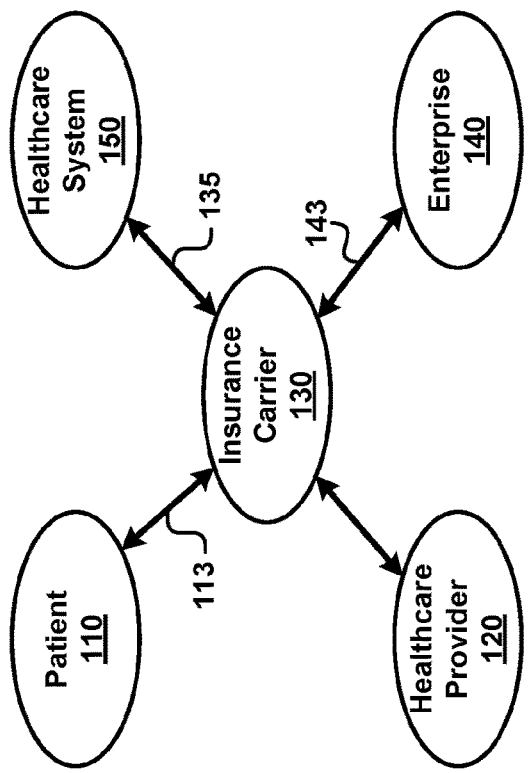

FIGS. 1A-1C depicts example environments in which several aspects of aiding triage management in healthcare systems can be implemented. The example environments are shown containing entities/elements such as patient 110, healthcare provider 120, insurance carrier 130, enterprise 140 and healthcare system 150. The elements are shown interconnected by data links 115, 125, 135, 145, etc.

Merely for illustration, only representative number/type of elements/links is shown in the Figure. Many environments often contain many more elements and/or links, both in number and type, depending on the purpose for which the environment is designed. Each element and data link of FIGS. 1A-1C is described below in further detail.

Patient 110 refers to a recipient of healthcare services. Information on patient 110 is commonly maintained in the form of electronic medical/health records (EMR/EHRs), as is well known in the relevant arts. EMR/EHRs (hereinafter referred commonly as EMRs) may specify details such as patient identity, dates of visit to avail healthcare services, symptoms of health problems faced by the patient, lab reports, etc.

Healthcare provider 120 refers to a physician/doctor, nurse, medical staff, care giver, etc. who provide one or more healthcare services to the patient. Healthcare providers are commonly associated with a healthcare organization (hospital, clinic, etc.) located at one or more geographical locations. Each healthcare provider commonly has responsibility for one or more patients.

Insurance carrier 130 represents an organization that offers various health insurance plans to patients, with each insurance plan being designed to protect the patient financially when health problems arise. In the below description, it is assumed that patient 110 has subscribed to at least one insurance plan offered by insurance carrier 130.

Enterprise 140 represents a third party organization that is related to providing healthcare or management services (e.g. customer relationship management). Enterprise 140 generally operates data and applications independent of the other elements noted here.

Healthcare system 150 represents a system that assists a healthcare organization in the delivery of healthcare services to patients. Healthcare system 150 aids in various healthcare aspects such as work-flow coordination between healthcare providers and patients, records (such as EMR) management, diagnosis, etc., as is well known in the relevant arts.

Referring to FIG. 1A, healthcare system 150 retrieves multiple parameters relating to a patient from different databases, the parameters including current and historical data relating to the patient. The current/historical data may be in the form of an EMR of the patient and may include patient information, symptoms of previous medical problems, details of visits, details of upcoming appointments, doctor's notes, observations, clinical summary, medications, patient documents and care plan, etc.

Healthcare system 150 may retrieve the EMR from an internal data store forming part of healthcare system 150. In one embodiment, healthcare system 150 sends a request for patient information via data link 145 to enterprise 140 and receives the EMR of the patient as a response to the request from enterprise 140 via data link 145. Multiple EMRs from different data stores may also be retrieved, with healthcare system 150 then forming a consolidated EMR of the patient from the retrieved data.

Healthcare system 150 then receives a request specifying the symptoms of a medical problem of the patient. In one embodiment, the request is received from healthcare provider 120 (via data link 125) such as a physician/doctor. The request may be received when the physician wants to review the status of his/her patients or in response to patient 110 coming for check-up/review with the physician, either in-house or as an out-patient at a premises of the healthcare organization as is well known.

In alternative embodiments, the request may be received from patient 110 via data link 115, for example, when patient 110 wishes to discuss health related issues such as symptoms, diagnosis, medicines, etc. with any healthcare providers of the healthcare organization. The request may also be received from insurance carrier 130 via data link 135 or from enterprise 140 via data link 145, for example, when the insurance carrier/enterprise wishes to review the condition of patient 110 with the healthcare providers related to the patient.

Healthcare system 150 determines based on the symptoms and the multiple retrieved parameters, recommendations to assist in the triage of patient 110 and provides (e.g. displayed on a display screen) the recommendations to healthcare provider 120 to assist in the triage of patient 110. Healthcare system 150 also provides recommendations that assist healthcare provider 120 in determining a probable diagnosis of the medical problem of patient 110. In one embodiment, healthcare system 150 also sends alerts to healthcare providers having responsibility for the patient upon determining that the triage of the patient matches a pre-determined threshold.

Referring to FIG. 1B, healthcare provider 120 sends a request (for example, using a client system) to healthcare system 150 specifying the symptoms of a medical problem of the patient. The request may be sent in response to receiving (via data link 112) a request from patient 110 for check-up/review with the healthcare provider. In alternative embodiments, the request may be sent in response to receiving corresponding requests for reviewing the condition of patient 110 from insurance carrier 130 (via data link 132) or from enterprise 140 (via data link 142).

Healthcare provider 120 then views the recommendations provided by healthcare system 150 and then perform the triage of patient 110. Specifically, healthcare provider 120 uses the recommendations to identify the level of urgency of patient 110. It should be noted that the recommendations are provided based on mining (analysis of) historical data of patient 110, and accordingly facilitate healthcare provider 120 to quickly and accurately identify the level of urgency.

Referring to FIG. 1C, insurance carrier 130 (a third-party different from the first party healthcare system 150 and the second party healthcare provider 120) retrieves multiple parameters relating to a patient from different databases, the parameters including current and historical data related to the patient. The current/historical data may be retrieved from healthcare system 150 (via data link 135) and/or enterprise 140 (via data link 143). Upon receiving a request from patient 110 (via data link 113), a request specifying the symptoms of a medical problem of the patient, insurance carrier 130 determines based on the symptoms and the multiple retrieved parameters, recommendations to assist in the triage of patient 110 and provides (e.g. displayed on a display screen) the recommendations to healthcare provider 120 to assist in the triage of patient 110.

Thus, the various entities/elements shown in FIGS. 1A-1C such as patient 110, healthcare provider 120, insurance carrier 130, enterprise 140 and healthcare system 150 operate to aid triage management in a healthcare system. The manner in which several features of the present disclosure can be implemented using a computing system (system architecture) is described below with examples.

2. System Architecture

Figure 2:
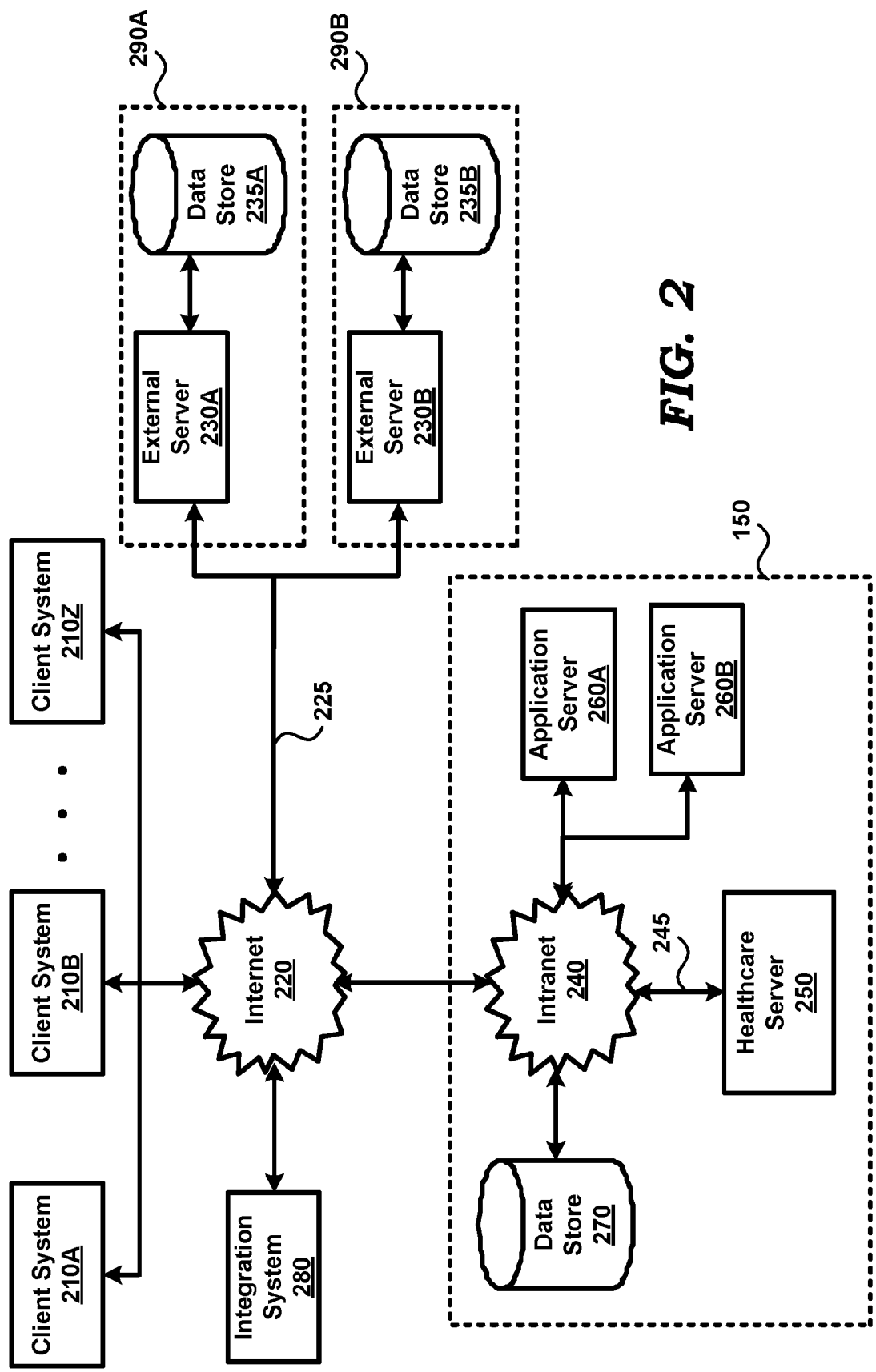
FIG. 2 is a block diagram of an example computing system in which several aspects of aiding triage management in healthcare systems can be implemented.

FIG. 2 is a block diagram of an example computing system in which several aspects of aiding triage management in healthcare systems can be implemented. The block diagram is shown containing client systems 210A-210Z, Internet 220, Intranet 240, external servers 230A-230B, data stores 235A-235B & 270, application servers 260A-260B, healthcare server 250 and integration system 280.

In one embodiment, healthcare server 250, application servers 260A-260B, and data store 270 along with intranet 240 operate together to as healthcare system 150 (as indicated by the dashed rectangle) that provides effective collaboration among various healthcare providers such as physicians/doctors, medical staff/nurse, care providers, etc.

Each of systems 290A (containing external server 230A and data store 235A) and 290B (containing external server 230B and data store 235B) represents a corresponding third-party external system with which healthcare system 150 interacts with to provide various aspects of the present disclosure. For example, external system 290A may represent a system provided by insurance carrier 130, with external server 230A being an insurance server belonging to insurance carrier 130. The insurance server may maintain (in data store 235A) information on patients having insurance coverage with insurance carrier 130. External system 290B may represent a system provided by enterprise 140, with external server 230B being an enterprise server belonging to enterprise 140.

Merely for illustration, only representative number/type of systems/devices are shown in the Figure. Many environments often contain many more systems and/or devices, both in number and type, depending on the purpose for which the environment is designed. Each system/device of FIG. 2 is described below in further detail.

Each of client systems 210A-210Z represents a system such as a personal computer, workstation, mobile station, mobile phones, computing tablets, etc., used by users/healthcare providers to send user requests to applications executing in healthcare system 150 (such as in application servers 260A-260B or healthcare server 250), and display the corresponding responses. The responses may be in the form of web pages and thus the requests may be in the form of Uniform Resource Locators (URLs) with appropriate additional content to specify the user requests. The users may generate the user requests based on appropriate user interfaces provided on each client system. In one embodiment, client systems 210A-210Z runs on different operating systems such as ANDROID™ and IOS™, and provide user interfaces using different web browser applications such as INTERNET EXPLORER®, SAFARI™, FIREFOX® and CHROME®.

Intranet 240 represents a network providing connectivity between application servers 260A-260B, healthcare server 250 and data store 270, all provided as part of healthcare system 150. Internet 220 extends the connectivity of these (and other systems of the healthcare system) with external systems such as client systems 210A-210Z and external systems 290A-290B. Each of intranet 240 and Internet 220 may be implemented using protocols such as Transmission Control Protocol (TCP) and/or Internet Protocol (IP), well known in the relevant arts. In general, in TCP/IP environments, an IP packet is used as a basic unit of transport, with the source address being set to the IP address assigned to the source system from which the packet originates and the destination address set to the IP address of the destination system to which the packet is to be eventually delivered.

A (IP) packet is said to be directed to a destination system when the destination IP address of the packet is set to the (IP) address of the destination system, such that the packet is eventually delivered to the destination system by Internet 220 and intranet 240. When the packet contains content such as port numbers, which specifies the destination application, the packet may be said to be directed to such application as well. The destination system may be required to keep the corresponding port numbers available/open, and process the packets with the corresponding destination ports. Each of Internet 220 and intranet 240 may be implemented using any combination of wire-based or wireless mediums.

Each of data stores 235A-235B and 270 represents a non-volatile (persistent) storage facilitating storage and retrieval of a collection of data by applications executing in corresponding server systems. For example, data store 270 facilitates applications executing in applications servers 260A-260B and healthcare server 250 to store/retrieve data related to patients, healthcare providers, the healthcare system, etc.

In one embodiment, each of data stores 235A-235B and 270 maintains information on patients in the form of EMRs. As noted above, EMRs may specify details of patients including patient identity, dates of visit, symptoms of medical problem faced by the patient, lab reports, patient records, etc. Each data store may also store the conversations of the participants of chat/interactive sessions between the various healthcare providers, the clinical data of the patients, etc.

Some of data stores 235A-235B and 270 may be implemented as a database server using relational database technologies and accordingly provide storage and retrieval of data using structured queries such as SQL (Structured Query Language). Some of data stores 235A-235B and 270 may be implemented as a file server providing storage and retrieval of data in the form of files organized as one or more directories, as is well known in the relevant arts.

Each of application servers 260A-260B, external servers 230A-230B and healthcare server 250 represents a server system, such as a web/application server, executing applications performing tasks requested by users (for example, using one of client systems 210A-210Z). Each server system may use data stored internally (for example, in a non-volatile storage/hard disk within the server system), external data (e.g., maintained in data store 235A-235B/270) and/or data received from external sources (e.g., from the user) in performing the requested tasks. The server system then sends the result of performance of the tasks to the requesting client system (e.g., one of 210A-210Z). The results may be accompanied by specific user interfaces (e.g., web pages) for displaying the results to the requesting user.

Integration system 280 represents a server system that that facilitates healthcare server 250 to interact with external systems 290A-290B. Integration system 280 may accordingly provide integration APIs (Application Programming Interface) containing a library of interfaces/protocols to external systems, an integration database for storing information sent/received from external systems, and a web server that facilitates interaction with external systems that operate with text based protocols such as Hyper Text Transfer Protocol Secure (HTTPS).

Healthcare server 250, provided according to several aspects of the present disclosure, aids in triage management of a large number of patients. The manner in which healthcare server 250 (and accordingly healthcare system 150) aids triage management is described below with examples.

3. General Flow

Figure 3:
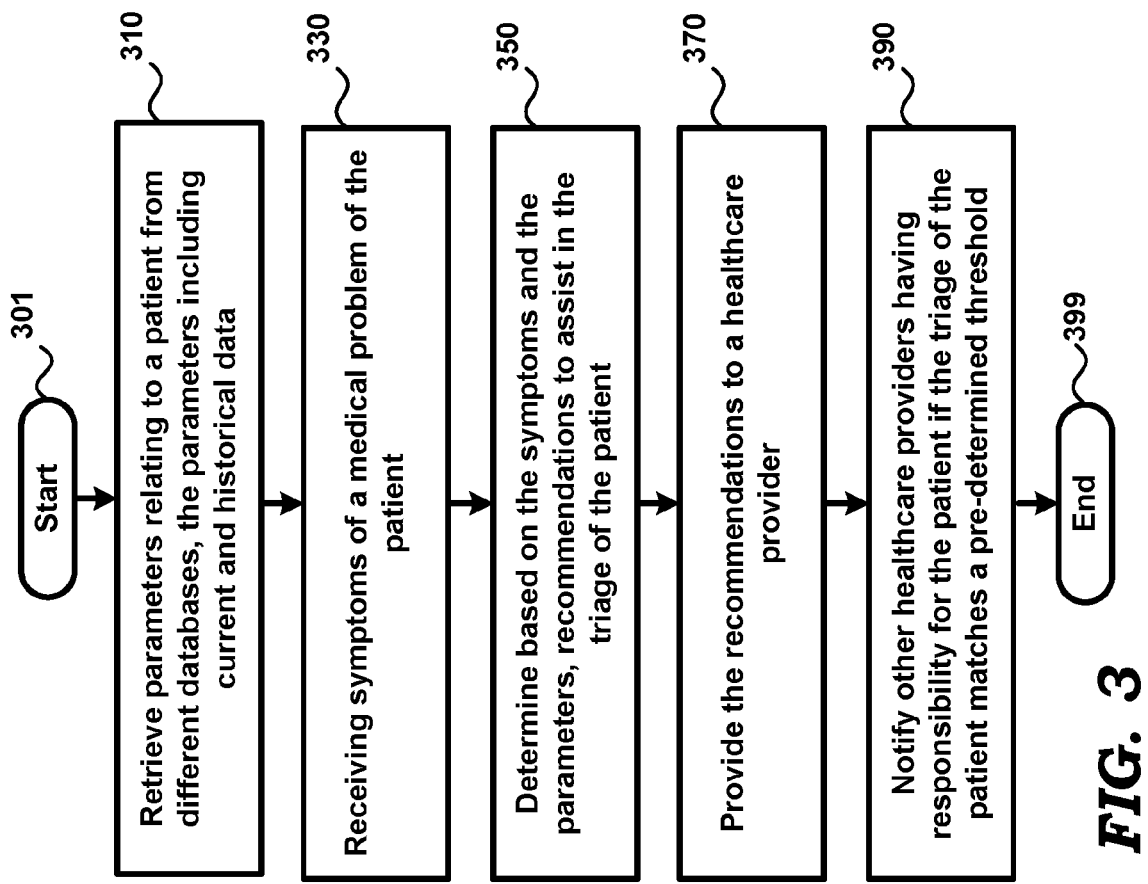
FIG. 3 is a flowchart illustrating the manner in which triage management is provided in a healthcare system according to an aspect of the present disclosure.

FIG. 3 is a flowchart illustrating the manner in which effective collaboration is provided in a healthcare system (150) according to an aspect of the present disclosure. The flowchart is described with respect to healthcare server 250 of FIG. 2 merely for illustration. However, the features can be implemented in other systems and environments also without departing from the scope and spirit of various aspects of the present disclosure, as will be apparent to one skilled in the relevant arts by reading the disclosure provided herein.

In addition, some of the steps may be performed in a different sequence than that depicted below, as suited to the specific environment, as will be apparent to one skilled in the relevant arts. Many of such implementations are contemplated to be covered by several aspects of the present disclosure. The flow chart begins in step 301, in which control immediately passes to step 310.

In step 310, healthcare server 250 retrieves parameters relating to a patient from different databases, the parameters including current and historical data of the patient. The current and historical data may be retrieved from a local store such as data store 270 or from external systems 290A-290B by interfacing with integration system 280.

In one embodiment, the different databases include but is not limited to (A) an electronic medical record (EMR) system storing EMRs linked to healthcare providers, each EMR containing information related to a corresponding patient, (B) a cloud database storing data captured using Internet of Things (IoT) devices associated with patients and (C) a monitoring database storing information collected by monitoring devices attached to the patients. Examples of monitoring devices include devices monitoring heart rate, blood pressure, diabetes levels, etc. of the patient.

The current and historical data include but is not limited to records of the patient, lab reports, data from IoT devices, data from monitoring devices, and clinical workflows available at multiple EMR systems. The records of the patient include patient information, symptoms of previous medical problems, details of visits, details of upcoming appointments, doctor's notes, observations, clinical summary, medications, patient documents and care plan.

In step 330, healthcare server 250 receives a request specifying symptoms of a medical problem of the patient. The request may be received from one of client systems 210A-210Z by a user/healthcare provider such as a physician/doctor. The request may be received when the physician wants to review the status of his patients or in response to a patient coming for check-up/review with the physician, either in-house or as an out-patient as is well known.

In one embodiment, healthcare server 250 enables the user/physician to specify the details of the current visit of the patient, for example, based on the physical inspection/testing of the patient. During the visit, the user/physician decides to triage the patient, for example, to determine the seriousness of the symptoms, to identify possible diagnosis and/or treatment of the patient. In the following description, it is assumed that the user/physician is using client system 210A to send the request specifying the symptoms.

In one embodiment, healthcare server 250 checks for validity of authentication details of the user/physician connecting via client system 210A. If authentication details of the user are found invalid, an authentication failed error message is displayed to the user. In addition, healthcare server 250 may allow the user to retry logging in for a predetermined number of times (which may be pre-configured). Control passes to step 350 if the authentication details of the user are found valid.

In step 350, healthcare server 250 determines based on the symptoms and the retrieved parameters, recommendations to assist in the triage of the patient. The determination may be performed in a known way. In one embodiment, healthcare server 250 first validates the data obtained from the different databases (those noted above). Validation refers to checking the data obtained for accuracy and consistency. Any desired checks may be performed as part of the validation. For example, the data retrieved from the different databases may be checked to determine a timeline of healthcare activities performed in relation to the reviewed patient and to discard any data that does not fit into the timeline.

Healthcare server 250 then performs data mining of the validated patient related data by applying standard and predictive algorithms. Some of the exemplary standard algorithms include Lexical Algorithm used for natural language processing; Format Preserve Caesar Cipher Algorithm used for data encryption and decryption; User-based Collaborative Filtering used for determining relevant recommendations; Linear Regression, Logistic Regression & Support Vector Machine used for Predictive Analytics; and Framingham Algorithm used for diabetic prediction.

In one embodiment, healthcare server 250 first determines whether an emergency is indicated for the patient based on the mining of the patient related information. Healthcare server 250 then determines whether any medical advice is to be provided for the patient based on the mining of the patient related information. Healthcare server 250 then performs symptom check on the collected data and provides recommendations and analysis to the healthcare provider interacting with the patient. Analysis typically involves applying predictive intelligence algorithms (noted above) to symptoms shown by the patient and historical data noted above to determine recommendations.

Some of the recommendations may include top three probable diagnosis, specialists who have treated such cases the most, most applicable diagnostics and drugs, etc. Healthcare server 250 also determines whether any recommendations (in addition to the medical advice) are to be provided for the patient based on the mining of the patient related information. Examples of additional recommendations include asking the patient to come for a review after a specific duration, to check with another specialist on a specific symptom, medical publications related to the symptoms of the patient, etc.

In step 370, healthcare server 250 provides the recommendations to the healthcare provider as a response to the request. In one embodiment, the recommendations are displayed on a display unit associated with client system 210A. According to an aspect of the present disclosure, the recommendations provided by the healthcare system also assist the healthcare provider in determining a probable diagnosis of the medical problem of the patient.

In step 390, healthcare server 250 notifies other healthcare providers having responsibility for the patient if the triage of the patient matches a pre-determined threshold. For example, during the mining of the patient related information, if healthcare server 250 determines that an emergency is indicated for the patient, healthcare server 250 sends emergency notifications to the doctor or a nurse station (client systems 210A-210Z). Emergency notifications typically notify appropriate medical staff (doctors and nursing staff) responsible for monitoring the patient indicating immediate attention and appropriate action. Exemplary emergency notifications include push notifications sent to a personal/mobile device of the doctor, sending alerts to a nurse station system, etc. Control then passes to step 399 where the flowchart ends.

It should be appreciated that the mining of the patient related current and historic data operate to assign a degree of urgency in treatment to the patient come in for a check-up with the healthcare provider, and in addition provides various recommendations and analysis in relation to the symptoms of the patient. For example, if details of a patient indicate emergency condition of the patient, then appropriate medical staff is notified by emergency alerts and accordingly is assigned a highest urgency level in the triage. Thus, healthcare server 250 (healthcare system 150) aids in triage management of patients.

It may be further appreciated that the healthcare system 150 may provide the above described features to client systems 210A-210Z in any convenient manner. In one embodiment, healthcare system 150 provides the various features as corresponding services as described below with examples.

4. Example Ecosystem of Services

Figure 4:
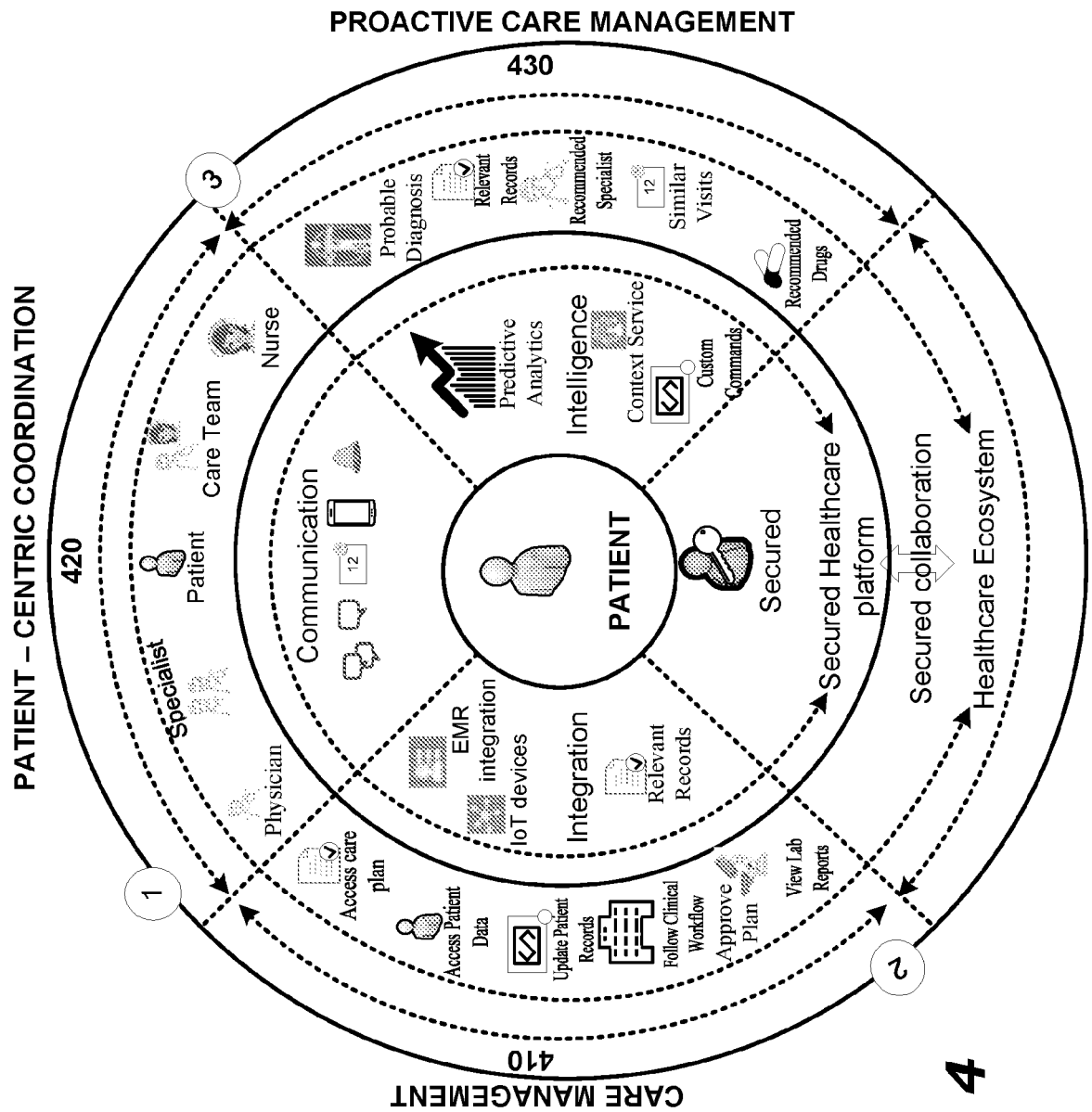
FIG. 4 illustrates an example ecosystem of services provided by a healthcare system in an embodiment.

FIG. 4 illustrates an example ecosystem of services provided by a healthcare system in an embodiment. The services provided by healthcare system 150 are broadly categorized into care management services 410, patient centric coordination services 420 and proactive care management services 430.

Care management services 410 include services such as Access care plan, Access Patient data, Update Patient Records, Follow Clinical Workflow, Approve Plan and View Lab Reports, which together facilitate management of care/treatment provided to patients. Care management services 410 may in turn employ integrations services such as CRM (customer relationship management) integration, EMR integration and IoT devices which facilitate patient data to be retrieved from/stored to external EMR/EHR systems.

Patient centric coordination services 420 facilitate the coordination between various healthcare providers such as patients, doctors (physicians), specialists, nursing staff and care team. Various types of collaborative communications may be employed for providing such coordination. Examples of such communication types include chats, Short Message Services (SMS), emails, Push Notifications, Emergency alerts, etc. According to an aspect of the present disclosure, specialists or doctors working at different hospitals associated with different EMRs are also facilitated to communicate/coordinate with each other.

Proactive care management services 430 include services such as Probable Diagnosis, Relevant Records, Recommended Specialists, Similar Visits and Recommended drugs that aid in triage management of patients. The proactive care management services may in turn employ intelligence services such as Predictive Analytics, Prescriptive Analytics, Adaptive Analytics, Context Service and Custom Commands which perform the analysis of patient relation information (symptoms and historical data) and determines the recommendations based on the analysis.

It may be appreciated that the services described above may be implemented by healthcare system 150 consistent with the environment (client systems, etc.) in which the healthcare system is sought to be deployed.

It may be further appreciated that the above features of the present disclosure may be provided by healthcare server 250 based on data maintained in data stores 235A-235B/270. Sample data that may be maintained in such data stores is described below with examples.

5. Sample Data

FIG. 5 depicts portions of a visit summary data specifying the details of interactions between patients and healthcare providers in one embodiment. For illustration, the visit summary data are assumed to be maintained in the form of tables in data store 270. However, in alternative embodiments, the visit summary data may be maintained according to other data formats (such as files according to extensible markup language (XML), etc.) and/or using other data structures (such as lists, trees, etc.), as will be apparent to one skilled in the relevant arts by reading the disclosure herein.

Table 500 depicts visit summary data specifying the details of visits of different patients to the healthcare organization. In particular, column 511 "Patient ID" specifies a unique identifier associated with a patient and column 512 "Patient Name" specifies the name of the patient. Columns 513 "HCP ID" and 514 "HCP Name" respectively specify a unique identifier and the name of the healthcare provider who attended to (and provided a corresponding healthcare service) to the patient.

Column 515 "Visit Date/Time" specifies the date and time of the visit of the patient, column 516 "Diagnosis" specifies the details of the diagnosis of the patient during the corresponding visit, column 517 "Urgency" specifies the details of the urgency determined for the patient (based on triage of the patient) and column 518 "Recommendation" specifies the details of the recommendations provided with respect to the corresponding visit of the patient. Only a sample number of columns is shown in table 500, though in alternative embodiments, a large number of additional columns may be present to indicate additional details of the visit of the patient.

Each of rows 541-547 specifies the details of a corresponding visit by patients. It may be readily observed that rows 542, 544 and 546 specify the details of the visits by the patient having identifier "PT4125" (name "Fienstein, Clara"). Similarly, other rows specify the details of visits of other patients.

In response to receiving a request specifying the symptoms of a patient (assumed to be "PT4125" named "Fienstein, Clara" for illustration), healthcare server 250 inspects the visit summary data of table 500 and determines the current and historic data related to the patient. As such, healthcare server 250 identifies the data in rows 542, 544 and 546 as being related to patient "PT4125". Healthcare server 250 then determines recommendations based on the symptoms and the historic data such as the data in the Diagnosis, Urgency and Recommendation columns in rows 542, 544 and 546.

Healthcare 250 also identifies healthcare providers having responsibility for the patient, that is, the healthcare providers who have treated the patient during earlier visits. As such, healthcare server 250 identifies the healthcare providers "HP052", "HP020" and "HP049" in rows 542, 544 and 546 as having responsibility for the patient "PT4125". Healthcare server 250 then sends notifications to one or more of these three healthcare providers based on the recommendations and diagnosis, if the triage of the patient matches a threshold level (e.g. emergency).

Thus, healthcare system 150 aids effective triage management of different patient using the visit summary data of table 500. The manner in which healthcare system 150 may be implemented is described below with examples.

6. Example Implementation

Figure 6:
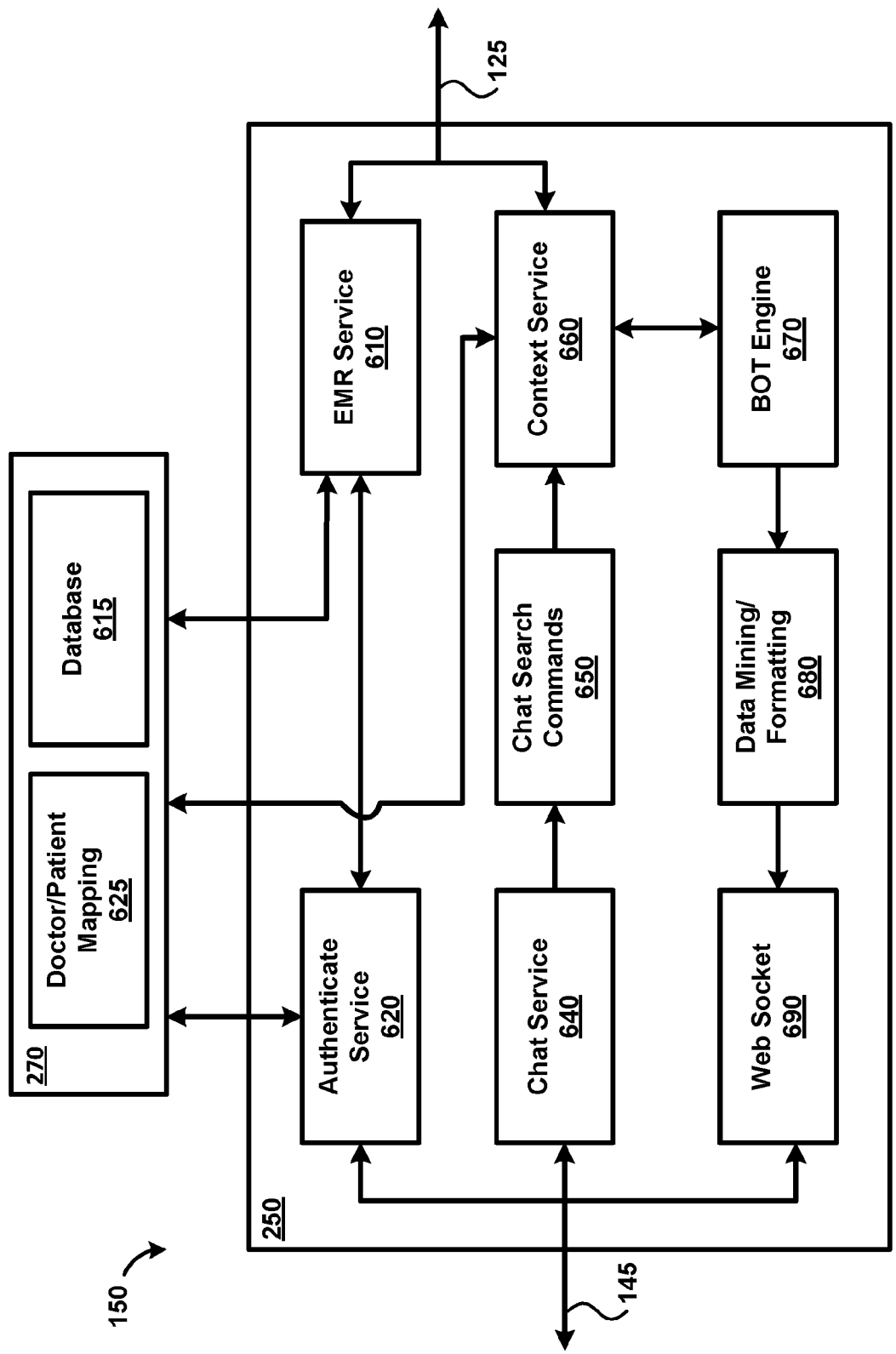
FIG. 6 is a block diagram illustrating an example implementation of a healthcare system.

FIG. 6 is a block diagram illustrating an example implementation of a healthcare system (150). The example implementation is shown in the form of a functional architecture containing multiple functional blocks implemented in various systems (such as healthcare server 250 and data store 270) belonging to healthcare system (150).

Healthcare server 250 is shown containing EMR service 610, authenticate service 620, chat service 640, chat search commands 650, context service 660, BOT engine 670, data mining/formatting 680 and web socket 690, while data store 270 is shown containing database 615 and doctor/patient mapping 625. It may be appreciated that in alternative embodiments, the various blocks/components may be implemented on multiple servers/data stores (which then together form healthcare system 150) as will be apparent to one skilled in the relevant arts. Each of the blocks of the healthcare system is described in detail below.

EMR service 610 facilitates accessing of data from external systems such as 290A-290B of FIG. 2. For example, EMR service 610 may interact with the external systems such as integration system 280 to request for authentication/authorization tokens for accessing the external EMR/EHR data. Such authentication tokens may be stored in database 615 and later used when accessing the external EMR/EHR data.

Database 615 facilitates storing/retrieving of data by other blocks in the healthcare system based on SQL queries. Some examples of data that may be maintained in database 615 include, but not limited to, authentication token from EMR service 610, authentication data of the users/healthcare providers from authenticate service 620, doctor/patient mapping data 625, chat history of the participants from chat service 640 and context data from context service 660.

Authenticate service 620 facilitates authentication and/or authorization of the users/healthcare providers to avail the services of the healthcare system of the present disclosure. Authenticate service 620 may employ standard authentication and/or authorization techniques well known in the relevant art such as Active Directory, Single Sign On, Database and LDAP. Furthermore, security technologies known in the relevant art (such as SSL) may be used by authenticate service 620 during authentication and/or authorization. Authenticate service 620 may maintain user related data in database 615 for providing the authentication and/or authorization service.

Doctor/patient mapping 625 represents a mapping (data) between patients and doctors such as list of doctors consulted by a patient and/or list of patients treated by a doctor. An example of such a mapping is the visit summary data shown in table 500 of FIG. 5. The doctor/patient mapping 625 may be updated periodically (for example, based on periodical examination of external EMR/EHR data). In addition, the mapping data may be updated by physician/healthcare providers during the visits by the patients.

Upon successful authentication and/or authorization of the user/healthcare provider, authenticate service 620 determines a list of patients handled by the authenticated user based on the information in doctor/patient mapping data 625 (as described in detail above). Authenticate service 620 then sends for display (for example, by sending the details to requesting client system 210A) the corresponding list of patients, thereby allowing the healthcare provider to access the profiles of his/her patients (including complete medical history, information related to last visit, appointments etc.).

Chat service 640 enables chat/collaboration among multiple participants of the healthcare system. Choosing/selecting a chat option for a particular patient enables an authenticated participant to discuss about a patient with other participants. In an example implementation, upon choosing the chat option, chat service 640 initiates a chat session by creating a group with all the participants (healthcare providers) having responsibility for the patient. Chat service 640 may use doctor-patient mapping data 625 for initiating the chat session. In addition, chat service 640 may store a chat history specifying the details of chats performed earlier in database 615. Chat service 640 also may identify and forward search commands issued by the participants during a chat session to chat search commands 650.

Chat search commands 650 enables the participants in a chat session to issue search commands for required information such as patient information, last vital information, patient/doctor visits, files etc. in chat history (stored in database 615) and/or external EMR/EHR databases and to and receive/view the results of the search commands. Chat search commands 650 may accordingly interact with context service 660 to perform the desired searches indicated by the issued search commands, receive the results of the searches and provide the results as corresponding responses to the issued search commands.

Context service 660 enables other blocks/components of healthcare system to retrieve required data from database 615 and and/or external EMR/EHR databases based on a context. The context may be related to a specific patient, a specific healthcare provider, and/or the specific background (e.g. triaging, chat, etc.) in which the context service has been requested. Context service 660 receives requests from chat search commands 650 or BOT engine 670 indicating the specific data to be retrieved. Context service 660 may then retrieve the specific data requested from database 615 and and/or external EMR/EHR databases (235A-235B) and forwards the retrieved data as corresponding responses to the requests.

BOT engine 670 provides an execution environment for executing bots/automated programs that perform a predefined set of actions, possibly by interacting with other systems such as client systems 210A-210Z. Some bots run automatically, while others only execute commands when they receive specific inputs. Examples of bots are web crawlers, chat room bots etc. Some of the bots may also facilitate predictive analytics using predictive algorithms. For example, in the field of healthcare, a patient info bot may pull the complete information/data of a patient from a database (which can be EMR/EHR and may act on the data to find some relevant/meaningful information and advice a doctor with suggestions about the areas of treatment).

In one embodiment, a chat bot (executing in BOT engine 670) performs predictive analytics (using predictive algorithms) on chat/collaboration history, chat context and commands given by participants during a chat/collaboration session, and render the results/suggestions to the participants. For example, when a participant sends a message (typically in the form of text) in a chat session indicating that a patient is suffering from high fever, headache, rash, muscle and joint pain, a chat bot may search for the symptoms in chat/collaboration history (related to all patients) and may thereafter arrive at the suggestion that the patient might be suffering from dengue fever (diagnosis). The chat bot may also suggest possible medications for the diagnosis.

Data mining/formatting 680 provides both mining and formatting services such as formatting/modifying the results of the predictive analytics of bot engine 670 according to the requirements of client systems 210A-210Z, and send the formatted output (e.g. in the form of a report) to the client systems via web socket 690, thereby enabling client systems 210A-210Z to render the formatted output to the participants.

In addition, data mining/formatting 680 may also inspect the data received from bot engine 670 and determine additional insights/suggestions using mining algorithms well known in the art. For example, data mining/formatting 680 may identify additional data to be included to the data received from bot engine 670.

Web socket 690, well-known in the relevant arts, is a computer communications protocol, providing full-duplex communication channels over a single TCP connection, and facilitates peer to peer and client-server communication. Web socket 690 facilitates the collaborative communication among the participants (here healthcare providers). Also, web socket 690 facilitates data mining/formatting 680 to send the results/suggestions received from bot engine 670 to participants using client systems 210A-210Z.

It may be appreciated that the various components of FIG. 6 facilitate a healthcare system (150) to provide several aspects of the present disclosure. Specifically, the various components of FIG. 6 operate together to implement the various services noted in FIG. 4. An example implementation of the Probable Diagnosis service shown as part of proactive care management services 430 is described in detail below.

In one embodiment, Probable Diagnosis service is implemented as a micro service listening on web socket 690, and accordingly receives a Symptoms Check request from (a web client executing in) client system 210A. The request may be sent after a healthcare provider (such as a doctor) has completed the physical review of the patient and entered the details of the symptoms in healthcare system 150. In an alternative embodiment, the request includes information about symptoms shown by patient or symptoms captured by devices monitoring the condition of the patient.

The Symptoms Check request is forwarded from web socket 690 to bot engine 670. As noted above, a patient info bot may be operative in bot engine 670, with the patient info bot performing the pre-defined actions of retrieving the patient information, mining the information to identify recommendations and analysis as described above with respect to step 350 of FIG. 3. The patient info bot executing in bot engine 670 sends a response to the request, with the response containing the medical advice recommendations and analysis.

The Probable Diagnosis service made available at web socket 690 forwards the response to (web client of) client system 210A. The recommendations and analysis received may thereafter be displayed to the healthcare provider on a display unit associated with client system 210A.

Thus, a service (Probable Diagnosis) is implemented by healthcare system 150. It may be appreciated that the other services of FIG. 4 may be similarly implemented by the operation of the various components of FIG. 6. The manner in which the various components of healthcare server 250 shown in FIG. 6 operate to provide effective triage management is described below with examples.

7. Sequence Diagram for Triage Management

Figure 7:
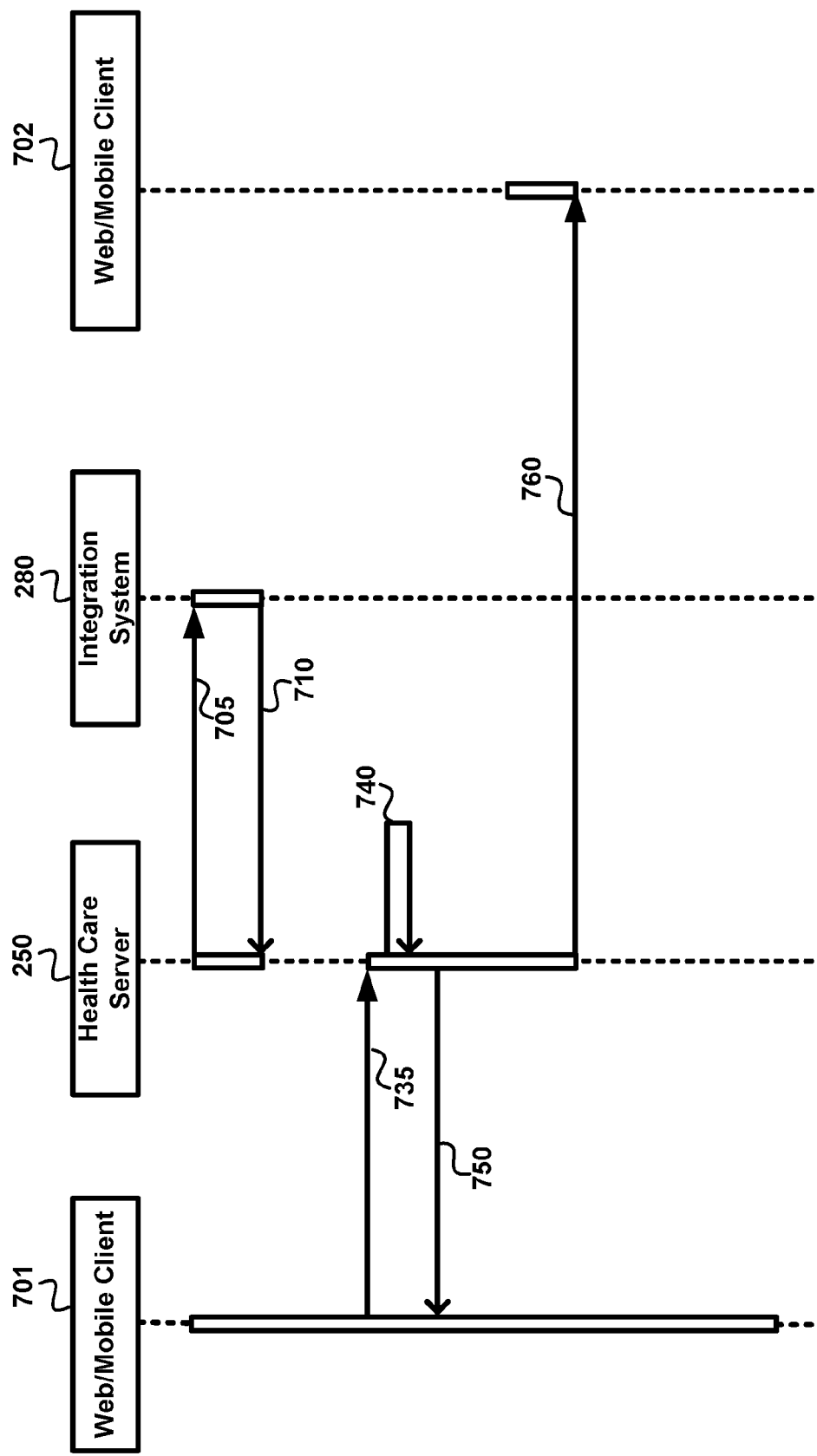
FIG. 7 is a sequence diagram illustrating the manner in which triage management is provided by a healthcare system in one embodiment.

FIG. 7 is a sequence diagram illustrating the manner in which triage management is provided by a healthcare system in one embodiment. The interactions are shown between web/mobile client 701 (executing in client system 210A), healthcare server 250, integration system 280 and web/mobile client 702 (executing in client system 210Z). The interactions are described in detail below.

At 705, healthcare server 250 sends a request to integration system 280, requesting access to data maintained in an external EMR/EHR database (such as 290A-290B) related to a patient. Integration system 280 may then interact with the external EMR/EHR database and obtain the requested data related to the patient. At 710, integration system 280 sends the requested data to healthcare server 250, using which healthcare server 250 is thereafter facilitated to perform data mining of the patient related information. Healthcare server 250 may store the retrieved patient related data in database 615 for subsequent usage.

Though not shown, it may be appreciated that healthcare server 250 may similarly interact with other systems such as a cloud database storing data captured using Internet of Things (IoT) devices associated with patients or a monitoring database storing information collected by monitoring devices attached to the patients and obtain the current and historical data related to a patient.

At 735, web/mobile client 701 sends a request specifying the symptoms of a medical problem of the patient to healthcare provider 250. At 740, healthcare provider 740 determines the recommendations based on the symptoms and the retrieved patient related historic data. At 750, healthcare provider 250 provides the recommendations to web/mobile client 701 so as to assist a healthcare provider (using web/mobile client 701) to triage the patient.

In the scenario that the recommendations include identifying the patient is in an emergency, healthcare provider 250 also sends alerts to other healthcare providers having responsibility of the patient. As such, at 760, healthcare provider 250 is shown sending an alert to web/mobile client 702 used by another healthcare provider having responsibility for the patient.

It may be appreciated that the operation of FIGS. 2 through 7 facilitates the healthcare system to provide effective triage management of patients.

It may be further appreciated that the features of the present disclosure are described above assuming that the healthcare system is implemented on a single server (healthcare server 250 of FIG. 2). However, healthcare systems are typically implemented using multiple servers and data stores. The manner in which a healthcare system may be provided using a cloud infrastructure is described below with examples.

8. Healthcare System Using Cloud Infrastructure

Figure 8:
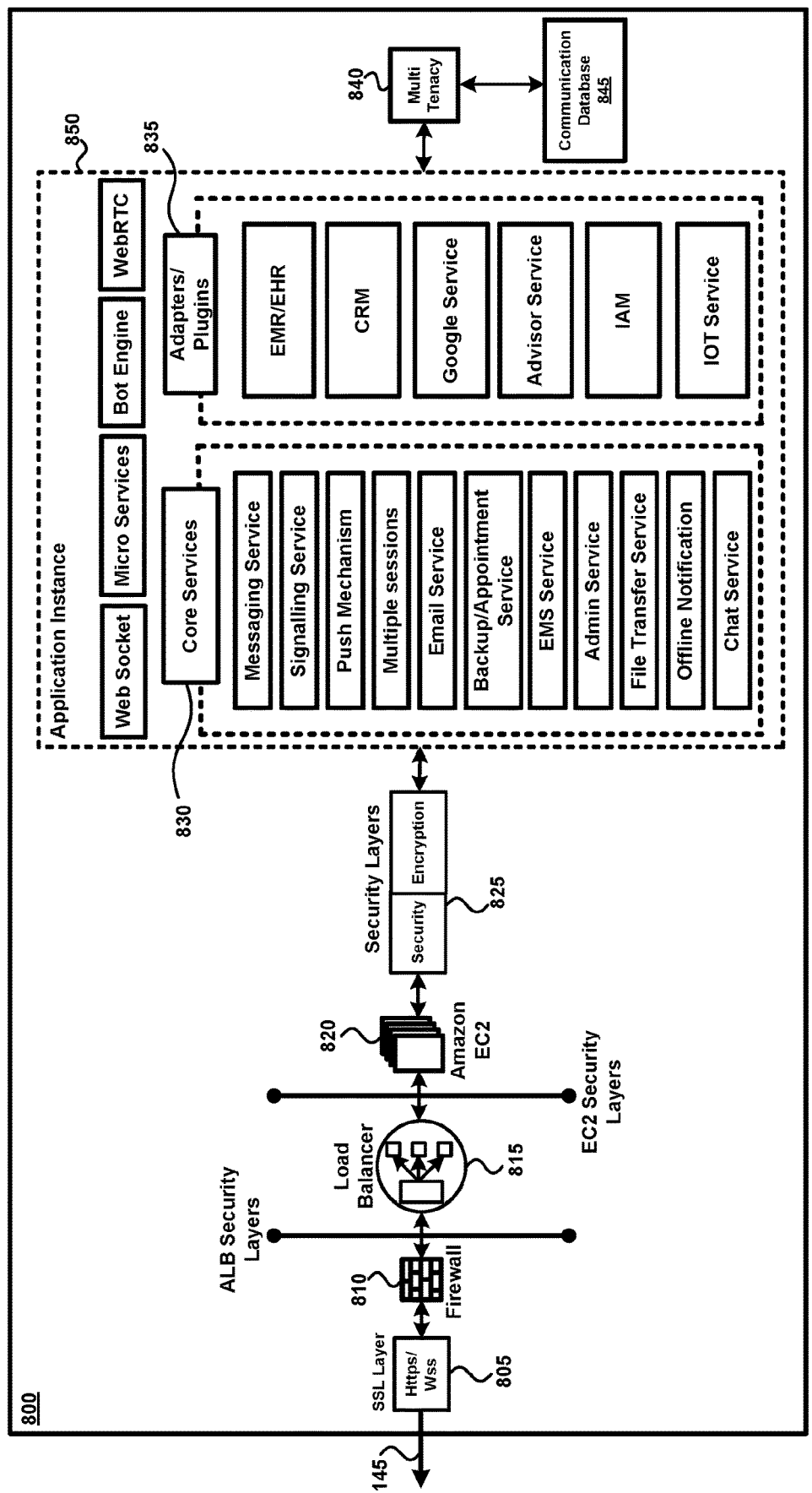
FIG. 8 is a block diagram illustrating the manner in which a healthcare system is provided using a cloud infrastructure in an embodiment.

FIG. 8 is a block diagram illustrating the manner in which a healthcare system is provided using a cloud infrastructure in an embodiment. Specifically, the healthcare system is shown implemented using AWS (Amazon Web Services) framework 800 available from Amazon™. Accordingly, the block diagram is shown containing SSL (Secure Sockets layer) 805, firewall 810, load balancer 815, Amazon Elastic Compute Cloud (Amazon EC2) 820, security layers 825, application server (instance) 850, and multi tenancy 840.

It should be appreciated that the healthcare system is implemented using multiple (typically, 50-100) application servers, though only a single application server 850 is shown in FIG. 8 for clarity.

SSL 805 is a standard security technology for establishing an encrypted link between application server 850 and any of client systems 210A-210Z. Firewall 810 is a network security device that monitors traffic to or from a network. Firewall 810 also allows or blocks traffic based on a defined set of security rules. Amazon EC2 820 is a web service that provides secure, resizable compute capacity on the cloud. Application Load Balancer (ALB) 815 distributes the user requests among the various application servers for reasons such as scalability, fault tolerance, etc. Security layers 825 provide additional level of security for the healthcare system in addition to SSL 805 and firewall 810. Multi tenancy 840 handles the tenancy of healthcare system in Amazon EC2 820.

Application server 850 is shown containing core services 830 and adapters/plugins 835 (in addition to associated components such as web socket, micro services and bot engine described above with respect to FIG. 6). Core services 830 facilitate the interaction among one or more application servers and also the interaction with client systems 210A-210Z, while adapters/plugins 835 facilitate application server to interact with external systems (via integration system 280). Some of core services 830 and adapters/plugins 835 are described in detail below.

Messaging service enables messages to be sent among application servers and/or client systems 210A-210Z. Such messages may be encrypted using user keys. Signaling service is used to provide audio/video calls for collaboration among participants on client systems 210A-210Z. Such audio/video calls may be provided using WebRTC, WebSocket and Amazon EC2 820. Push mechanism pushes messages such as alerts or emergency notifications to the client system used by the appropriate user (here doctor/nursing staff). Multiple sessions service enables a user to login into multiple client systems simultaneously. Email service enables a user to compose and send emails including any attachments or recordings, if any.

Backup/appointment service enables user to assign another user as back up (in cases of emergency) on his/her unavailability. In addition, backup/appointment service sends alerts or emergency notifications to another user assigned as back up. Furthermore, backup/appointment service enables recording of appointments for patient's consultations. As an example, recording of appointments includes modifying date, time and doctor mapped for consultation.

EMS (Enterprise Messaging Service) service provides multi factor authentications of users. For example, a two factor authentication (two levels of verification) of login details of a user may be provided. Details of such two levels of verification are sent via emails, SMS (Short Messaging Service), etc. Admin service enables a user to fetch data from PHI (Protected Health Information) systems via integration system 280. File transfer service enables a user to send/share documents to another user in real time, for example, during collaboration. In addition, file transfer service may encrypt the documents before sending/sharing.

Offline notification service sends alerts to a user notifying emergency when client systems 210A-210Z are in offline mode. Offline notification service uses Firebase or Apple Push Notification Service (APNs) to send the alerts, for example, in the form of alarm beeps. Chat service enables chat based collaboration among multiple participants including sending of private messages, creating chat rooms/groups and storing the chat history.

EMR/EHR adapter enables retrieving of EMR of patients from external EMR/EHR systems via integration system 280. Exemplary data in EMR includes Patient documents, medications, Patient info, care plan, doctor notes, observations, clinical summary and visits details. CRM adapter facilitates data to be retrieved from an external CRM system via integration system 280. Google™ service adapter facilitates application server 850 to interface with Google™ services. Advisor service adapter facilitates interactions with third party bots to retrieve suggestions and recommendations. IAM (Identity and Access Management) adapter facilitates interactions with external servers to perform authentication and/or authorization of the users/healthcare providers in the healthcare system.

IoT service adapter facilitates interactions with IoT devices such as heart monitors. Such interaction may facilitate application server 850 to determine whether heart beat of a patient monitored through an IoT device records a lower value or a higher value than the standard thresholds, and then send an alert to the appropriate medical staff (nurse/doctor).

Additional components such as Micro services, WebRTC, Web sockets and Bot engine may be associated with application server 850. Micro services are back end services or self-sustained services and these can be any plug and play services. For example, in healthcare industry, the micro services render the patient data required by the doctors. WebRTC ((Web Real-Time Communication) provides web browsers and mobile applications with real-time communication (RTC) via simple application programming interfaces (APIs). WebRTC allows audio and video communication to work inside web pages by allowing direct peer-to-peer communication, eliminating the need to install plugins or download native apps. Web socket and Bot engine are described above with respect to FIG. 6.

Communication database 845 represents a non-volatile (persistent) storage facilitating storage and retrieval of data by applications executing in other systems such as application server 850. Communication database 845 may be implemented as a database server using relational database technologies and accordingly provide storage and retrieval of data using structured queries such as SQL (Structured Query Language). Alternatively, or in addition, communication database 845 may be implemented as a file server providing storage and retrieval of data in the form of files organized as one or more directories, as is well known in the relevant arts.

It should be appreciated that the features described above can be implemented in various embodiments as a desired combination of one or more of hardware, executable modules, and firmware. The description is continued with respect to an embodiment in which various features are operative when executable modules are executed.

9. Digital Processing System

Figure 9:
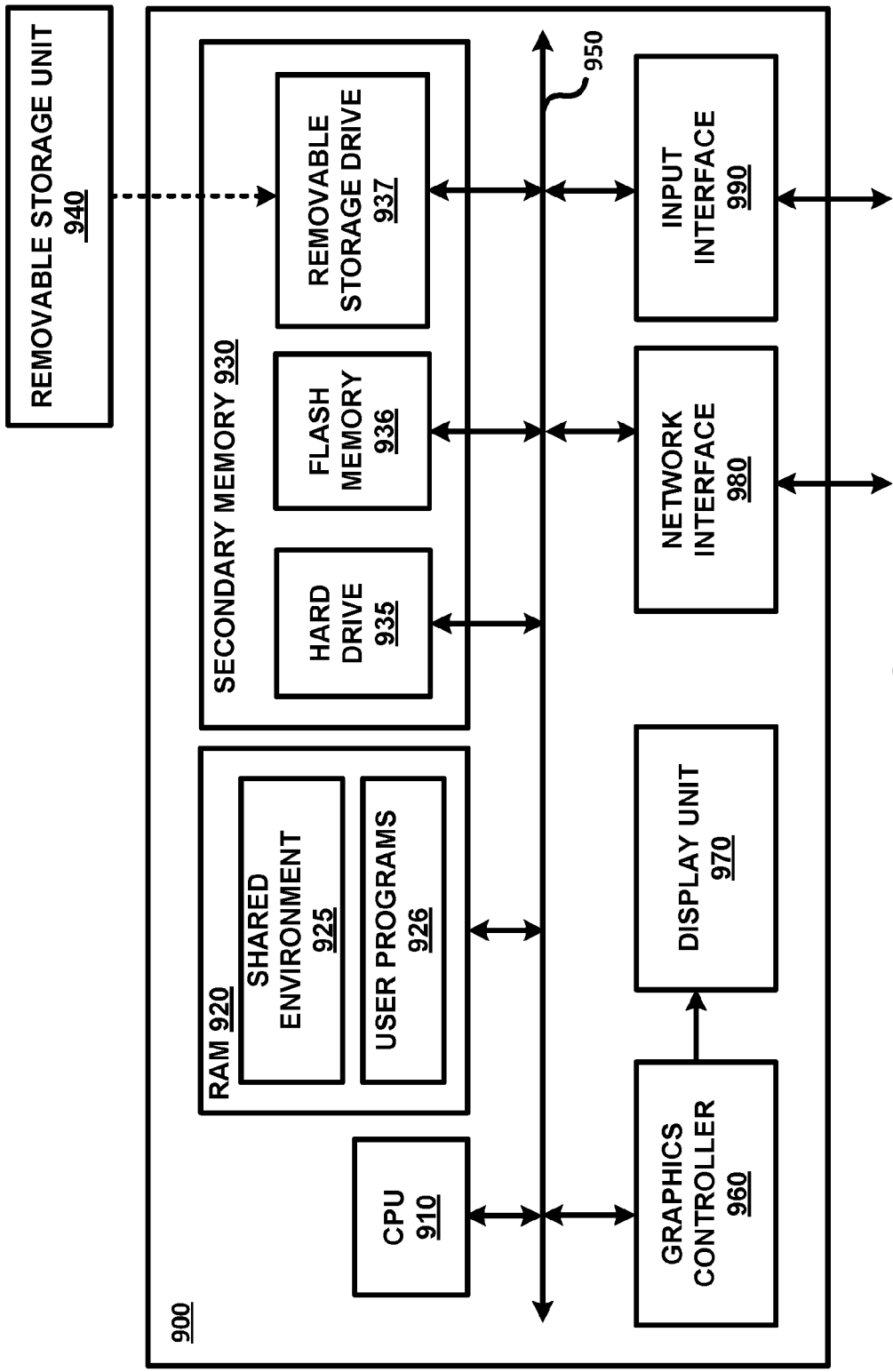
FIG. 9 is a block diagram illustrating the details of a digital processing system in which various aspects of the present disclosure are operative by execution of appropriate executable modules.

FIG. 9 is a block diagram illustrating the details of digital processing system 900 in which various aspects of the present disclosure are operative by execution of appropriate executable modules. Digital processing system 900 corresponds to healthcare server 250 or application server 850.

Digital processing system 900 may contain one or more processors such as a central processing unit (CPU) 910, random access memory (RAM) 920, secondary memory 930, graphics controller 960, display unit 970, network interface 980, and input interface 990. All the components except display unit 970 may communicate with each other over communication path 950, which may contain several buses as is well known in the relevant arts. The components of FIG. 9 are described below in further detail.

CPU 910 may execute instructions stored in RAM 920 to provide several features of the present disclosure. CPU 910 may contain multiple processing units, with each processing unit potentially being designed for a specific task. Alternatively, CPU 910 may contain only a single general-purpose processing unit.

RAM 920 may receive instructions from secondary memory 930 using communication path 950. RAM 920 is shown currently containing software instructions constituting shared environment 925 and user programs 926. Shared environment 925 includes operating systems, device drivers, virtual machines, etc., which provide a (common) run time environment for execution of user programs 926.

Graphics controller 960 generates display signals (e.g., in RGB format) to display unit 970 based on data/instructions received from CPU 910. Display unit 970 contains a display screen to display the images defined by the display signals. Input interface 990 may correspond to a keyboard and a pointing device (e.g., touch-pad, mouse) that may be used to provide appropriate inputs. Network interface 980 provides connectivity to a network (e.g., using Internet Protocol), and may be used to communicate with other systems (of FIG. 1) connected to the network.

Secondary memory 930 may contain hard drive 935, flash memory 936, and removable storage drive 937. Secondary memory 930 may store the data (for example, portions of visit summary data of FIG. 5) and software instructions (for implementing the flowchart of FIG. 3, the services of FIG. 4, and to provide several features of the present disclosure), which enable digital processing system 900 to provide several features in accordance with the present disclosure. The code/instructions stored in secondary memory 930 either may be copied to RAM 920 prior to execution by CPU 910 for higher execution speeds, or may be directly executed by CPU 910.

Some or all of the data and instructions may be provided on removable storage unit 940, and the data and instructions may be read and provided by removable storage drive 937 to CPU 910. Removable storage unit 940 may be implemented using medium and storage format compatible with removable storage drive 937 such that removable storage drive 937 can read the data and instructions. Thus, removable storage unit 940 includes a computer readable (storage) medium having stored therein computer software and/or data. However, the computer (or machine, in general) readable medium can be in other forms (e.g., non-removable, random access, etc.).

In this document, the term "computer program product" is used to generally refer to removable storage unit 940 or hard disk installed in hard drive 935. These computer program products are means for providing software to digital processing system 900. CPU 910 may retrieve the software instructions, and execute the instructions to provide various features of the present disclosure described above.

The term "storage media/medium" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as secondary memory 930. Volatile media includes dynamic memory, such as RAM 920. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 950. Transmission media can also take the form of acoustic or light waves, such as those generated during radio-wave and infra-red data communications.

Reference throughout this specification to "one embodiment", "an embodiment", or similar language means that a particular feature, structure, or characteristic described in connection with the embodiment is included in at least one embodiment of the present disclosure. Thus, appearances of the phrases "in one embodiment", "in an embodiment" and similar language throughout this specification may, but do not necessarily, all refer to the same embodiment.

Furthermore, the described features, structures, or characteristics of the disclosure may be combined in any suitable manner in one or more embodiments. In the above description, numerous specific details are provided such as examples of programming, software modules, user selections, network transactions, database queries, database structures, hardware modules, hardware circuits, hardware chips, etc., to provide a thorough understanding of embodiments of the disclosure.

10. Conclusion

While various embodiments of the present disclosure have been described above, it should be understood that they have been presented by way of example only, and not limitation. Thus, the breadth and scope of the present disclosure should not be limited by any of the above-described exemplary embodiments, but should be defined only in accordance with the following claims and their equivalents.

It should be understood that the figures and/or screen shots illustrated in the attachments highlighting the functionality and advantages of the present disclosure are presented for example purposes only. The present disclosure is sufficiently flexible and configurable, such that it may be utilized in ways other than that shown in the accompanying figures.

Further, the purpose of the following Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the present disclosure in any way.

What is claimed is:
1. A method comprising:
 interacting, via a healthcare system, with an integration system and requesting for a first authentication token;
 receiving, via the healthcare system, a command requesting information on a patient along with the first authen- tication token, retrieving information and forwarding the command requesting information on the patient to the integration system;

automatically determining, via the integration system, that the first authentication token is valid and requesting for a second authentication token when the first authentication token is invalid;

retrieving, via the healthcare system, context data comprising a plurality of parameters relating to the patient from a plurality of external and internal databases by interfacing with the integration system when one of the first authentication token and the second authentication token is valid, the parameters comprising current and historical data relating to the patient, wherein the integration system obtains the context data from the plurality of external and internal databases and communicates to the healthcare system;

forming, via the healthcare system, a consolidated electronic medical record, using a plurality of electronic medical records of the patient, retrieved from the plurality of external and internal databases;

receiving, via the healthcare system, symptoms of a medical problem of the patient;

determining, via the healthcare system, based on the symptoms, a timeline of healthcare activities performed in relation to the patient and filtering the plurality of parameters to find relevant parameters;

determining, via the healthcare system, based on the symptoms and the relevant parameters, a degree of urgency in treatment and a recommendation to assist in triage of the patient; and providing, via the healthcare system, the degree of urgency and the recommendation to a healthcare provider to assist in the triage of the patient;

wherein the context data can be at least one of a patient specific data, a healthcare provider specific data, and a medical problem specific data;

wherein the recommendation is provided based on predictive analytics, prescriptive analytics, adaptive analytics, and collaborative filtering on at least one of a chat, a collaboration history, a chat context, commands given by participants during the chat, and the consolidated electronic medical record of the patient to render treatment suggestions and insights to the participants and the consolidated electronic medical record of the patient;

wherein the healthcare system is configured to provide the recommendation using a predictive algorithms by searching for symptoms in at least one of the chat, and the collaboration history and arrive at the treatment suggestions and insights regarding at least one of diagnosis that the patient is suffering, and medications for the diagnosis, based on a message by the participants in a chat session; and wherein the method is configured to aid triage management by the healthcare system.

2. The method of claim 1, wherein the recommendation also assists in determining a probable diagnosis of the medical problem.

3. The method of claim 2, wherein the recommendation also includes (A) diagnostics to be performed for confirmation of the probable diagnosis, (B) drugs suitable for a treatment of the probable diagnosis, and (C) specialist healthcare providers having experience in the treatment of the probable diagnosis.

4. The method of claim 2, further comprising sending alerts to the healthcare provider having responsibility for the patient upon determining that the triage of the patient matches a pre-determined threshold.

5. The method of claim 1, wherein the plurality of external and internal databases comprises (A) an electronic medical record system storing electronic medical records linked to the healthcare provider, each electronic medical record containing information related to a corresponding patient, (B) a cloud database storing data captured using Internet of Things (IoT) devices associated with the patient and (C) a monitoring database storing information collected by monitoring devices attached to the patient.

6. The method of claim 5, wherein the current and historical data comprise records of the patient, lab reports, data from IoT devices, data from monitoring devices, and clinical workflows available at multiple electronic medical record systems.

7. The method of claim 6, wherein the records of the patient comprise patient information, symptoms of previous medical problems, details of visits, details of upcoming appointments, doctor's notes, observations, clinical summary, medications, patient documents and care plan.

8. A tangible non-transitory machine-readable medium comprising instructions executable by a processor for implementing an operation in a healthcare system for aiding triage management, the operation comprises:

interacting, via the healthcare system, with an integration system and requesting for a first authentication token;

receiving, via the healthcare system, a command requesting information on a patient along with the first authentication token, retrieving information and forwarding the command requesting information on the patient to the integration system;

automatically determining, via the integration system, that the first authentication token is valid and requesting for a second authentication token when the first authentication token is invalid;

retrieving, via the healthcare system, context data comprising a plurality of parameters relating to the patient from a plurality of external and internal databases by interfacing with the integration system when one of the first authentication token and the second authentication token is valid, the parameters comprising current and historical data relating to the patient, wherein the integration system obtains the context data from the plurality of external and internal databases and communicates to the healthcare system;

forming, via the healthcare system, a consolidated electronic medical record, using a plurality of electronic medical records of the patient, retrieved from the plurality of external and internal databases;

receiving, via the healthcare system, symptoms of a medical problem of the patient;

determining, via the healthcare system, based on the symptoms, a timeline of healthcare activities performed in relation to the patient and filtering the plurality of parameters to find relevant parameters;

determining, via the healthcare system based on the symptoms and the relevant parameters, a degree of urgency in treatment and a recommendation to assist in triage of the patient; and providing, via the healthcare system, the degree of urgency and the recommendation to a healthcare provider to assist in the triage of the patient;

wherein the context data can be at least one of a patient specific data, a healthcare provider specific data, and a medical problem specific data; and wherein the recommendation is provided based on predictive analytics, prescriptive analytics, adaptive analytics, and collaborative filtering on at least one of a chat, a collaboration history, a chat context, commands given by participants during the chat, and the consolidated electronic medical record of the patient to render treatment suggestions and insights to the participants and the consolidated electronic medical record of the patient;

wherein the healthcare system is configured to provide the recommendation using a predictive algorithms by searching for symptoms in at least one of the chat, and the collaboration history and arrive at the treatment suggestions and insights regarding at least one of diagnosis that the patient is suffering, and medications for the diagnosis, based on a message by the participants in a chat session.

9. The non-transitory machine-readable medium of claim 8, wherein the recommendation also assists in determining a probable diagnosis of the medical problem.

10. The non-transitory machine-readable medium of claim 9, wherein the recommendation also includes (A) diagnostics to be performed for confirmation of the probable diagnosis, (B) drugs suitable for a treatment of the probable diagnosis, and (C) specialist healthcare providers having experience in the treatment of the probable diagnosis.

11. The non-transitory machine-readable medium of claim 9, the operation further comprises sending alerts to the healthcare provider having responsibility for the patient upon determining that the triage of the patient matches a pre-determined threshold.

12. The non-transitory machine-readable medium of claim 11, wherein the external and internal plurality of databases comprises (A) an electronic medical record system storing electronic medical records linked to the healthcare provider, each electronic medical record containing information related to a corresponding patient, (B) a cloud database storing data captured using Internet of Things (IoT) devices associated with the patient and (C) a monitoring database storing information collected by monitoring devices attached to the patient.

13. The non-transitory machine-readable medium of claim 12, wherein the current and historical data comprise records of the patient, lab reports, data from IoT devices, data from monitoring devices, and clinical workflows available at multiple electronic medical record systems.

14. The non-transitory machine-readable medium of claim 13, wherein the records of the patient comprise patient information, symptoms of previous medical problems, details of visits, details of upcoming appointments, doctor's notes, observations, clinical summary, medications, patient documents and care plan.

15. A digital processing system comprising:
a memory to store instructions; a processor to execute the instructions stored in the memory to cause the digital processing system to perform actions of:
interacting, via the digital processing system, with an integration system and requesting for a first authentication token;
receiving, via the digital processing system, a command requesting information on a patient along with the first authentication token, retrieving information and forwarding the command requesting information on the patient to the integration system;
automatically determining, via the integration system, that the first authentication token is valid and requesting for a second authentication token when the first authentication token is invalid;
retrieving, via the digital processing system, context data comprising a plurality of parameters relating to the patient from a plurality of external and internal databases by interfacing with the integration system when one of the first authentication token and the second authentication token is valid, the parameters comprising current and historical data relating to the patient, wherein the integration system obtains the context data from the plurality of external and internal databases and communicates to a healthcare system;
forming, via the digital processing system, a consolidated electronic medical record, using a plurality of electronic medical records of the patient, retrieved from the external and internal plurality of databases;
receiving, via the digital processing system, symptoms of a medical problem of the patient; determining, via the digital processing system, based on the symptoms, a timeline of healthcare activities performed in relation to the patient and filtering the plurality of parameters to find relevant parameters;
determining, via the digital processing system, based on the symptoms and the relevant parameters, a degree of urgency in treatment and a recommendation to assist in a triage of the patient; and
providing, via the digital processing system, the degree of urgency and the recommendation to a healthcare provider to assist in the triage of the patient;
wherein the context data can be at least one of a patient specific data, a healthcare provider specific data, and a medical problem specific data; and
wherein the recommendation is provided based on predictive analytics, prescriptive analytics, adaptive analytics, and collaborative filtering on at least one of a chat, a collaboration history, a chat context, commands given by participants during the chat, and the consolidated electronic medical record of the patient to render treatment suggestions and insights to the participants and the consolidated electronic medical record of the patient;
wherein the healthcare system is configured to provide the recommendation using predictive algorithms by searching for symptoms in at least one of the chat, and the collaboration history and arrive at the treatment suggestions and insights regarding at least one of diagnosis that the patient is suffering, and medications for the diagnosis, based on a message by the participants in a chat session; and
wherein the digital processing system is configured to aid triage management of the patient.

16. The digital processing system of claim 15, wherein the recommendation also assists in determining a probable diagnosis of the medical problem.

17. The digital processing system of claim 16, wherein the recommendation also includes (A) diagnostics to be performed for confirmation of the probable diagnosis, (B) drugs suitable for a treatment of the probable diagnosis, and (C) specialist healthcare providers having experience in the treatment of the probable diagnosis.

18. The digital processing system of claim 16, further performing the actions of sending alerts to the healthcare provider having responsibility for the patient upon determining that the triage of the patient matches a pre-determined threshold.

19. The digital processing system of claim 18, wherein the plurality of external and internal databases comprises (A) an electronic medical record system storing electronic medical records linked to the healthcare provider, each electronic medical record containing information related to a corresponding patient, (B) a cloud database storing data captured using Internet of Things (IoT) devices associated with the patient and (C) a monitoring database storing information collected by monitoring devices attached to the patient.

20. The digital processing system of claim 19, wherein the current and historical data comprise records of the patient, lab reports, data from IoT devices, data from monitoring devices, and clinical workflows available at multiple electronic medical record systems, wherein the records of the patient comprise patient information, symptoms of previous medical problems, details of visits, details of upcoming appointments, doctor's notes, observations, clinical summary, medications, patient documents and care plan.

* * * * *